US008475820B2

(12) United States Patent
Kuzma et al.

(10) Patent No.: US 8,475,820 B2
(45) Date of Patent: Jul. 2, 2013

(54) METHOD OF MANUFACTURING AN IMPLANTABLE DEVICE

(75) Inventors: Petr Kuzma, Princeton, NJ (US); Stefanie Decker, Princeton, NJ (US); Harry Quandt, Bensalem, PA (US)

(73) Assignee: Endo Pharmaceuticals Solutions Inc., Malvern, PA (US)

( * ) Notice: Subject to any disclaimer, the term of this patent is extended or adjusted under 35 U.S.C. 154(b) by 249 days.

(21) Appl. No.: 12/844,357

(22) Filed: Jul. 27, 2010

(65) Prior Publication Data

US 2010/0292144 A1    Nov. 18, 2010

Related U.S. Application Data

(62) Division of application No. 12/490,971, filed on Jun. 24, 2009, now Pat. No. 8,071,537.

(60) Provisional application No. 61/075,625, filed on Jun. 25, 2008.

(51) Int. Cl.
*A61F 2/02*    (2006.01)

(52) U.S. Cl.
USPC ........................................... 424/422

(58) Field of Classification Search
None
See application file for complete search history.

(56) References Cited

U.S. PATENT DOCUMENTS

| | | | |
|---|---|---|---|
| 2,513,014 A | 6/1950 | Fields |
| 3,921,632 A | 11/1975 | Bardani |
| 4,131,604 A | 12/1978 | Szycher |
| 4,285,987 A | 8/1981 | Ayer et al. |
| 4,298,002 A | 11/1981 | Ronel et al. |
| 4,386,039 A | 5/1983 | Szycher |
| 4,523,005 A | 6/1985 | Szycher |
| 4,743,673 A | 5/1988 | Johnston et al. |
| 4,751,133 A | 6/1988 | Szycher et al. |
| 4,846,793 A | 7/1989 | Leonard et al. |
| 4,871,094 A | 10/1989 | Gall et al. |
| 4,954,587 A | 9/1990 | Mueller |
| 4,959,217 A | 9/1990 | Sanders et al. |
| 4,994,028 A | 2/1991 | Leonard et al. |
| 5,004,614 A | 4/1991 | Staniforth |
| 5,035,891 A | 7/1991 | Runkel et al. |
| 5,254,662 A | 10/1993 | Szycher et al. |
| 5,266,325 A | 11/1993 | Kuzma et al. |
| 5,273,752 A | 12/1993 | Ayer et al. |
| 5,292,515 A | 3/1994 | Moro et al. |
| 5,342,622 A | 8/1994 | Williams et al. |
| 5,354,835 A | 10/1994 | Blair |
| 5,431,921 A | 7/1995 | Thombre |
| 5,464,933 A | 11/1995 | Bolognesi et al. |
| 5,468,811 A | 11/1995 | Moro et al. |
| 5,614,223 A | 3/1997 | Sipos |
| 5,637,309 A | 6/1997 | Tajima et al. |
| 5,686,411 A | 11/1997 | Gaeta et al. |
| 5,756,127 A | 5/1998 | Grisoni et al. |
| 5,817,343 A | 10/1998 | Burke |
| 5,854,127 A | 12/1998 | Pan |
| 5,876,761 A | 3/1999 | Bodmer et al. |
| 5,894,458 A | 4/1999 | Takizawa et al. |
| 6,087,334 A | 7/2000 | Beeley et al. |
| 6,143,718 A | 11/2000 | Kolterman et al. |
| 6,159,490 A | 12/2000 | Deghenghi |
| 6,313,254 B1 | 11/2001 | Meijs et al. |
| 6,337,318 B1 | 1/2002 | Trigg et al. |
| 6,361,797 B1 | 3/2002 | Kuzma et al. |
| 6,417,164 B1 | 7/2002 | Kolterman et al. |
| 6,579,851 B2 | 6/2003 | Goeke et al. |
| 6,602,694 B1 | 8/2003 | Albrandt et al. |
| 6,770,623 B1 | 8/2004 | Chang et al. |
| 6,872,700 B1 | 3/2005 | Young et al. |
| 6,942,264 B1 | 9/2005 | Mendez |
| 6,969,480 B2 | 11/2005 | Dalton et al. |
| 7,008,927 B2 | 3/2006 | Ochiai et al. |
| 7,056,887 B2 | 6/2006 | Coolidge et al. |
| 7,101,853 B2 | 9/2006 | Young et al. |
| 7,105,489 B2 | 9/2006 | Hathaway |
| 7,115,569 B2 | 10/2006 | Beeley et al. |
| 7,118,737 B2 | 10/2006 | Kochendoerfer et al. |
| 7,153,825 B2 | 12/2006 | Young et al. |
| 7,220,721 B1 | 5/2007 | Beeley et al. |
| 7,259,136 B2 | 8/2007 | Hathaway et al. |
| 7,271,238 B2 | 9/2007 | Gaeta et al. |
| 7,452,868 B2 | 11/2008 | Kuzma et al. |
| 2002/0141985 A1 | 10/2002 | Pittner et al. |
| 2003/0036504 A1 | 2/2003 | Kolterman et al. |
| 2003/0162862 A1 | 8/2003 | McCabe et al. |
| 2004/0002454 A1 | 1/2004 | Coolidge et al. |
| 2004/0071736 A1 | 4/2004 | Quinn et al. |

(Continued)

FOREIGN PATENT DOCUMENTS

EP    0 246 653 A2    11/1987
EP    0 314 206 B1    5/1989

(Continued)

OTHER PUBLICATIONS

Vintas (histrelin implant), published in 2004, Reference ID: 2887911.*

(Continued)

*Primary Examiner* — Gyan Chandra
(74) *Attorney, Agent, or Firm* — RatnerPrestia (57) ABSTRACT

Described herein are implantable devices, formulations and methods of making implantable devices for the release of a polypeptide from an implantable device, and methods of use thereof.

8 Claims, 1 Drawing Sheet

U.S. PATENT DOCUMENTS

| | | | |
|---|---|---|---|
| 2004/0097419 A1 | 5/2004 | Petersen et al. |
| 2005/0037078 A1 | 2/2005 | Kuo et al. |
| 2005/0079216 A1 | 4/2005 | Petereit et al. |
| 2005/0143303 A1 | 6/2005 | Quay et al. |
| 2005/0287320 A1 | 12/2005 | Dalton et al. |
| 2006/0019903 A1 | 1/2006 | Kuzma |
| 2006/0030528 A1 | 2/2006 | Hathaway et al. |
| 2006/0035836 A1 | 2/2006 | Coolidge et al. |
| 2006/0067911 A1 | 3/2006 | Nilsson et al. |
| 2006/0122106 A1 | 6/2006 | Gedulin et al. |
| 2006/0148713 A1 | 7/2006 | Beeley et al. |
| 2006/0204540 A1 | 9/2006 | Kuzma et al. |
| 2006/0233747 A1 | 10/2006 | Kochendoerfer et al. |
| 2006/0293232 A1 | 12/2006 | Levy et al. |
| 2007/0010656 A1 | 1/2007 | Beeley et al. |
| 2007/0037897 A1 | 2/2007 | Wang et al. |
| 2008/0311170 A1 | 12/2008 | Kuzma et al. |
| 2009/0035343 A1 | 2/2009 | Kuzma et al. |
| 2009/0087470 A1 | 4/2009 | Kuzma et al. |

FOREIGN PATENT DOCUMENTS

| | | |
|---|---|---|
| EP | 0 384 646 A1 | 6/1993 |
| EP | 0 551 699 A1 | 7/1993 |
| EP | 0 645 136 A2 | 3/1995 |
| FR | 821383 A | 12/1937 |
| GB | 1 306 541 A | 2/1973 |
| JP | 05-269759 A | 10/1993 |
| JP | 05-269760 A | 10/1993 |
| JP | 07-097338 A | 4/1995 |
| JP | 07-252166 A | 10/1995 |
| JP | 11-506730 A | 6/1999 |
| JP | 2002-535452 A | 10/2002 |
| NZ | 245383 | 5/1994 |
| WO | WO-96/40049 A1 | 12/1996 |
| WO | WO-98/44964 A1 | 10/1998 |
| WO | WO-00/44356 | 8/2000 |
| WO | WO-02/49573 A2 | 6/2002 |
| WO | WO-02/078597 A2 | 10/2002 |
| WO | WO-2004/071736 A2 | 8/2004 |
| WO | WO-2005/013936 A2 | 2/2005 |
| WO | WO-2005/041873 A2 | 5/2005 |
| WO | WO-2006/099288 A3 | 9/2006 |
| WO | WO-2007/028394 A2 | 3/2007 |
| WO | WO-2008/061355 A1 | 5/2008 |
| WO | WO-2008/134475 A2 | 11/2008 |

OTHER PUBLICATIONS

International Preliminary Report on Patentability received for PCT/US2009/048475 dated Jan. 5, 2011.
Non-final Office Action received for U.S. Appl. No. 12/490,971 dated Feb. 2, 2011.
Notice of Allowance received for U.S. Appl. No. 12/490,979 dated Feb. 4, 2011.
Shi et al., Expert Opin. Drug Deliv., "Current Advances in Sustained-Release Systems for Parenteral Drug Delivery," vol. 2(6), 2005, pp. 1039-1058.
U.S. Appl. No. 12/490,979, filed Jun. 24, 2009, Kuzma et al.
"RxMed: Pharmaceutical Information-Sandostatin LAR DEPOT" [online], Jan. 6, 2003 [retrieved Aug. 16, 2006]; http://www.rxmed.com.
Barradell, L. B. et al., "Histrelin: A Review of its Pharmacological Properties and Therapeutic Role in Central Precocious Puberty," Drugs, vol. 45, No. 4, Apr. 1993, pp. 570-588; published by Adis International Limited.
Berge, et al., "Pharmaceutical Salts," Journal of Pharmaceutical Sciences, vol. 66, No. 1, Jan. 1977, pp. 1-19.
Bevan et al., Primary Medical Therapy for Acromegaly: An Open, Prospective, Multicenter Study of the Effects of Subcutaneous and Intramuscular Slow-Release Octreotide on Growth Hormone, Insulin-Like Growth Factor-L, and Tumor Size, J. Clin. Endoc. Metab,. 87(10), 2002, pp. 4554-4563.
Chinese Office Action corresponding to CN 2006800160292, dated Sep. 4, 2009, 8 pages.
Eurasian Patent Office Decision on Patentability corresponding to EU 200701956/28, dated Jan. 21, 2009, 6 pages.
New Zealand Patent Office Examination Report corresponding to NZ 561400, dated Jul. 28, 2009, 2 pages.
Feuillan, P. P. et al., "Follow-up of children and young adults after GnRH-agonist therapy for central precocious puberty," J. Endocrinol. Invest., vol. 24, 2001, pp. 734-736; published by Editrice Kurtis.
Higuchi, et al., Pro-Drugs as Novel Drug Delivery Systems: A.C.S Symposium Series, American Chemical Society, Washington, DC, 1975.
International Search Report and Written Opinion, PCT/US2009/050215, dated Nov. 25, 2009, 11 pgs.
International Search Report, PCT/US00/01664, dated Jul. 13, 2000, 1 pg.
International Search Report, PCT/US06/08891, dated Dec. 4, 2006, 2 pgs.
International Search Report, PCT/US2005/021368, dated Oct. 23, 2006, 3 pgs.
International Search Report, PCT/US2008/061511, dated Nov. 8, 2009, 2 pgs.
Lan NaLee, "Volume of Blood in a Human," from http://hypertextbook.com/facts/1998/LanNaLee.shtml, (1998) updated (2001).
Langer, "Implantable Controlled Release Systems," Pharmac. Ther. (1983), vol. 21, p. 35-51.
M. F. Refojo, et al., "Microscopic Desternination of the Penetration of Proteins and Polysaccharides into Poly(hydroxyethyl Methacrylate) and similar Hydrogels," Journal of Polymer Science, Polymer Symposium, vol. 66, (1979), pp. 227-237.
P. E. Nielsen et al., "Peptide Nucleic Acid (PNA). A DNA Mimic with a Peptide Backbone," Bioconjugate Chem., vol. 5, No. 1, 1994, pp. 3-7.
P. Kuzma et al., U.S. PTO Office Action, U.S. Appl. No. 11/155,822 dated Jan. 22, 2008, 12 pgs.
P. Kuzma et al., U.S. PTO Office Action, U.S. Appl. No. 11/155,822 dated Feb. 18, 2009, 11 pgs.
P. Kuzma et al., U.S. PTO Office Action, U.S. Appl. No. 11/155,822 dated Oct. 13, 2009, 21 pgs.
Remington's Pharmaceutical Sciences, Osol., A. ed., Mack Publishing Co., (1980).
Roche, ed., Bioreversible Carriers in Drug Design: Theory and Application, Pergamon Press, New York, 1987.
S. W. Kim et al., "Water in Polymers—Solute Permeation Through Hydrogel Membranes," ACS Symposium Series, 127 (1980), pp. 347-359.
American Peptide Company, Inc., Peptide Catalog 2006-2007, pp. 119, 171, 175, 211, 217, 219, 227, 296, 315, 317 and 329.
Bodmer D., et al: "Factors influencing the release of peptides and proteins from biodegradable parenteral depot systems" Journal of Controlled Release, Elsevier, Amsterdam, NL LNKD-DOI:10.1016/0168-3659(92)90014-1, vol. 21, No. 1-3, Jul. 1, 1992, pp. 129-137, XP025702099 ISSN: 0168-3659 [retrieved on Jul. 1, 1992].
European Search Report for EP/00904513, completed Mar. 27, 2003.
European Search Report for EP/92300394, completed Sep. 28, 1992.
European Search Report for EP/92300395, dispatched Feb. 27, 1995.
Final Office Action on U.S. Appl. No. 11/155,822, mail date Jul. 8, 2010.
International Search Report for PCT/US2009/048475, dated Jun. 1, 2010.
International Search Report and Written Opinion for PCT/US2009/048484 dated Nov. 26, 2009.
Non-final Office Action for U.S. Appl. No. 11/372,749 dated Feb. 5, 2008.
Non-final Office Action on U.S. Appl. No. 12/490,979 dated Sep. 29, 2010.
Non-final Office Action for U.S. Appl. No. 12/490,971, mailed Sep. 21, 2010.
Notice of Allowance for U.S. Appl. No. 12/240,690, mail date Mar., 26, 2010.
Notice of Allowance for U.S. Appl. No. 11/372,749 dated Aug. 11, 2008.
Notice of Allowance for U.S. Appl. No. 12/171,999, mail date Mar. 22, 2010.

O'Donnell, et al "Therapeutic Potential of a Long Acting Somatostatin Analogue in Gastrointestinal Diseases" GUT, 1989, vol. 30, pp. 1165-1172.

Office Action for U.S. Appl. No. 07/589,957, mail date Oct. 17, 1991.

Palii et al., "Medical treatment of diabetic retinopathy with somatostatin analogues," Expert Opinion Investig. Drugs, vol. 16, No. 1, (2007), pp. 73-82.

Pawlikowski et al., "Perspectives of new potential therapeutic applications of somatostatin analogs," Neuroendocrinology Letters, vol. 24, Nos. 1/2, Feb.-Apr., 2003, pp. 21-27.

Pierard-Franchimont et al., "Incidental Control of Rosacea by Somatostatin," Dermatology, (2003) 206:249-251.

Prommer, "Established and Potential Therapeutic Applications of Octreotide in Palliative Care", Support Care Cancer, 2008, vol. 16, pp. 1117-1123.

Spitz, et al. "GnRH Superanalog Implants for Prostate Cancer" Proceedings of the 12th International Congress of Endocrinology, 2004, pp. 389-395.

Supplementary European Search Report for EP/67838004, completed Jun. 23, 2010.

Non-final Office Action received for U.S. Appl. No. 12/109,852 dated Oct. 6, 2011.

Notice of Allowance on U.S. Appl. No. 12/490,971 dated Jun. 9, 2011.

Examination Report for European Application No. EP 09 770 945.5 Dated Feb. 23, 2012.

* cited by examiner

METHOD OF MANUFACTURING AN IMPLANTABLE DEVICE

CROSS REFERENCE TO RELATED APPLICATIONS

This application is a divisional of U.S. patent application Ser. No. 12/490,971 filed on Jun. 24, 2009, which in turn claims the benefit of U.S. Provisional Application No. 61/075,625, filed Jun. 25, 2008, both of which are incorporated herein by reference in their entirety for any and all purposes.

BACKGROUND

The sustained release of active agents, e.g., exenatide, is known to be of value. In particular, long-term drug delivery has been shown to be effective in obtaining constant serum levels and in improving patient compliance.

Hydrogel membranes may be used for sustained delivery of active compounds. There are several theories regarding the mechanism of solute diffusion in hydrogels. The hydrogels that have been described have some porosity due to the network structure of the crosslinked polymer chains, which allow smaller molecules to diffuse through the structure. The size of the pores varies depending upon the hydrogel chemical composition and thus its degree of hydration. The hydrogels described in the art, however, are not particularly well adapted for delivery of large macromolecules, including bioactive proteins useful for the therapeutic treatment of humans and animals.

There is a need for delivery devices that provide controlled delivery of therapeutically effective amounts of bioactive polypeptides, which can be utilized in the treatment of a variety of diseases and pathological conditions in humans and animals.

SUMMARY

Described herein are devices, methods and reagents for the controlled release of bioactive polypeptides, including, for example, exenatide, and for the preparation of implantable devices useful for the controlled release of such polypeptides. Described herein are also devices, methods and reagents useful for treating particular diseases or disorders.

One embodiment is directed to an implantable device for the sustained release of a polypeptide, comprising: a) a homogeneous copolymer matrix that, in a hydrated state, forms a hydrogel with an equilibrium water content value ranging from about 20% to about 85%, wherein the homogeneous copolymer matrix further comprises a release agent of a molecular weight of at least about 1000 Daltons; and b) a solid formulation comprising a polypeptide, wherein the solid formulation is substantially encased within the homogeneous copolymer matrix. In a particular embodiment, the release agent comprises a non-ionic surfactant, e.g., one selected from the group consisting of: Brij 35, polyoxyethylene(20)sorbitan trioleate, Tween 20, Tween 80, Vitamin E TPGS, and combinations thereof. In a particular embodiment, the implantable device has an outer surface area of about 350 mm$^2$ or greater when in a dry state, e.g., from about 350 mm$^2$ to about 600 mm$^2$. In a particular embodiment, the implantable device has an outer surface area of about 500 mm$^2$ or greater when in a hydrated state, e.g., from about 500 mm$^2$ to about 800 mm$^2$. In a particular embodiment, the polypeptide comprises a GLP-1 analogue, e.g., exenatide. In a particular embodiment, the homogeneous copolymer is formed using a formulations of Table 2. In a particular embodiment, the solid formulation comprises about 98% exenatide and about 2% stearic acid.

One embodiment is directed to a method of delivering a polypeptide to a subject in a sustained release manner, the method comprising inserting an implantable device beneath the subject's skin, wherein the implantable device comprises a homogeneous copolymer matrix comprising a release agent with a molecular weight of at least about 1000 Daltons, and a solid formulation comprising a polypeptide, wherein the solid formulation is substantially encased within the matrix. The device can be inserted in a dry or hydrated state. In a particular embodiment, the implantable device provides a sustained release of the polypeptide over a period of at least about two months. In a particular embodiment, the release agent comprises a non-ionic surfactant, e.g., one selected from the group consisting of: Brij 35, polyoxyetheylene(20) sorbitan trioleate, Tween 20, Tween 80, Vitamin E TPGS, and combinations thereof. In a particular embodiment, the implantable device has an outer surface area of about 350 mm$^2$ or greater when in a dry state, e.g., from about 350 mm$^2$ to about 600 mm$^2$. In a particular embodiment, the implantable device has an outer surface area of about 500 mm$^2$ or greater when in a hydrated state, e.g., from about 500 mm$^2$ to about 800 mm$^2$. In a particular embodiment, the polypeptide comprises a GLP-1 analogue, e.g., exenatide. In a particular embodiment, the homogeneous copolymer is formed using a formulations of Table 2. In a particular embodiment, the solid formulation comprises about 98% exenatide and about 2% stearic acid. In a particular embodiment, the subject is diabetic or in need of glycemic control.

One embodiment is directed to a method of treating a diabetic subject, comprising inserting an implantable device under the diabetic subject's skin, wherein the implantable device comprises a homogeneous copolymer matrix comprising a release agent with a molecular weight of at least about 1000 Daltons, and a solid formulation comprising a polypeptide selected from the group consisting of: a GLP-1 analog, exenatide, liraglutide, and analogs thereof, wherein the solid formulation is substantially encased within the copolymer matrix. In a particular embodiment, the device provides a release on a daily basis an effective amount of the polypeptide over a period of at least about three months, at least about six months or at least about twelve months.

One embodiment is directed to a method of treating a subject in need of glycemic control, comprising inserting beneath a hypoglycemic or hyperglycemic subject's skin an implantable device comprising a homogeneous copolymer matrix, and a solid formulation comprising a polypeptide selected from the group consisting of exenatide, liraglutide, and analogues thereof, which is substantially encased within said matrix; and allowing said device to release on a daily basis an effective amount of said polypeptide over a period of at least about three months, at least about six months or at least about twelve months. In a particular embodiment, the matrix includes a release agent having a molecular weight of at least about 1000.

One embodiment is directed to a method of manufacturing an implantable device, wherein the implantable device can deliver a therapeutic polypeptide agent to a subject, and the release of the therapeutic polypeptide agent from the implantable device can be modulated by varying the components or the amounts of the components of the implantable device, the method comprising: a) mixing one or more polymerizable monomeric substances; b) adding one or more substances selected from the group consisting of: an excipient, a wetting agent, a non-ionic surfactant, an organic solvent, an alcohol, a reducing agent, an oxidizing agent and an aqueous solvent; and c) subjecting the mixture to conditions that cause the one or more polymerizable monomeric substances to polymerize in the presence of the one or more components, thereby forming the implantable device. In a particular embodiment, the one or more polymerizable monomeric substances comprises one or more compounds selected from the group consisting of: 2-hydroxyethyl methacrylate, ethyleneglycol dimethacrylate, and trimethylolpropane trimethacrylate. In a particular embodiment, the mixture further comprises one or more components selected from the group consisting of: benzoin methyl ether, Perkadox 16, and isopropyl alcohol. In a particular embodiment, the rate of release of the therapeutic polypeptide can be modulated. In a particular embodiment, the mixture is placed into a mold prior to being subjected to a polymerization step. In a particular embodiment, the polymerization step is initiated by ultraviolet irradiation. In a particular embodiment, the method(s) of manufacturing an implantable device further comprise charging or loading the implantable device with a desired amount of a therapeutic polypeptide agent. In a particular embodiment, the therapeutic polypeptide agent comprises a GLP-1 analog, e.g., exenatide. In a particular embodiment, the therapeutic polypeptide agent is combined with a wetting agent to form a solid formulation prior to being charged into the implantable device. In a particular embodiment, the solid formulation comprises about 98% exenatide and about 2% stearic acid.

One embodiment is directed to an implantable device that is formed using a mixture of about 78.72% HEMA, about 0.40% EGDMA, about 0.79% Vitamin E TDGS, about 0.24% BME, about 0.08% P-16, about 9.89% water and about 9.89% isopropyl alcohol.

One embodiment is directed to an implantable device that is formed using a mixture of about 78.72% HEMA, about 0.40% EGDMA, about 0.79% Vitamin E TDGS, about 0.24% BME, about 0.08% P-16 and about 19.78% water.

One embodiment is directed to an implantable device that is formed using a mixture of about 68.97% HEMA, about 0.35% EGDMA, about 0.69% Vitamin E TDGS, about 0.21% BME, about 0.07% P-16, about 14.85% water and about 14.85% isopropyl alcohol.

One embodiment is directed to an implantable device that is formed using a mixture of about 68.97% HEMA, about 0.35% EGDMA, about 0.69% Vitamin E TDGS, about 0.21% BME, about 0.07% P-16 and about 29.71%.

DETAILED DESCRIPTION

Before the present compositions and methods are described, it is to be understood that they are not limited to the particular molecules, compositions, methodologies or protocols described, as these may vary. It is also to be understood that the terminology used in the description is for the purpose of describing the particular versions or embodiments only, and is not intended to limit the scope of the present invention, which will be limited only by the appended claims. The terms used herein have meanings recognized and known to those of skill in the art, however, for convenience and completeness, particular terms and their meanings are set forth below.

The singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments described herein, the preferred methods, devices, and materials are now described. All publications mentioned herein are incorporated by reference to the extent they support the present invention. Nothing herein is to be construed as an admission that the invention is not entitled to antedate such disclosure by virtue of prior invention.

As used herein, the term "about" means plus or minus 10% of the numerical value of the number with which it is being used. For example, about 50% means in the range of 40%-60%.

"Controlled-release formulation" refers to a formulation designed to consistently release a predetermined, therapeutically effective amount of drug or other active agent such as a polypeptide or a synthetic compound over an extended period of time, with the result being a reduction in the number of treatments necessary to achieve the desired therapeutic effect. As described herein, a controlled formulation decreases the number of treatments necessary to achieve the desired effect. The controlled-release formulations achieve a desired pharmacokinetic profile in a subject, preferably commencement of the release of the active agent substantially immediately after placement in a delivery environment, followed by consistent, sustained, preferably zero-order, substantially zero-order, or near-zero order release of the active agent.

As used herein, the term "controlled-release" includes the predetermined, consistent release of active agent from the dosage formulation at a rate such that a therapeutically beneficial blood level below toxic levels of the active agent is maintained over a period, for example, of at least about two months, about six months or more (e.g., up to about two years).

The terms "patient" and "subject" mean all animals including humans. Examples of patients or subjects include humans, cows, dogs, cats, goats, sheep and pigs.

The term "pharmaceutically acceptable salts, esters, amides, and prodrugs" as used herein refers to those carboxylate salts, amino acid addition salts, esters, amides, and prodrugs of the compounds of the present invention that are, within the scope of sound medical judgment, suitable for use in contact with the tissues of patients without undue toxicity, irritation, allergic response and the like. Their use is commensurate with a reasonable benefit/risk ratio, and is effective for their intended use. Zwitterionic forms, where possible, can also be used. The compounds described herein can exist, for example, in unsolvated and solvated forms with pharmaceutically acceptable solvents such as, for example, water, ethanol and the like. In general, the solvated forms are considered equivalent to the unsolvated forms for the purposes of the present invention.

The term "prodrug" refers to compounds that are rapidly transformed in vivo to yield the parent compounds of the above formula, for example, by hydrolysis in blood. A discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These can include cations based on the alkali and alkaline earth metals, such as sodium, lithium, potassium, calcium, magnesium, and the like, as well as non-toxic ammonium, tetramethylammonium, tetraethylammonium, methylamine, dimethylamine, trimethylamine, triethylamine, ethylamine and the like (See, for example, S. M. Barge et al., "Pharmaceutical Salts," *J. Pharm. Sci.*, 1977, 66:1-19, which is incorporated herein by reference in its entirety).

The terms "active agent" or "drug" as used herein includes any agent that can be delivered to produce a clinically useful result. For the purposes described herein, the active agent or drug is a polypeptide that can be delivered from an implantable device to produce the desired clinical effect. The active agents, whether in solid or liquid form, have sufficient solubility or miscibility in an aqueous system to render them capable of being released through the hydrogel membranes into the delivery environment. Active agents include, but are not limited to, synthetic as well as natural polypeptides and their analogues, and include those polypeptides that are physiologically or pharmacologically active ("bioactive polypeptide") and produce a localized or a systemic effect in animals. Polypeptide active agents, for example, can have glucoregulatory effects such as lowering blood glucose levels, improving glucose control, suppressing pancreatic glucagon release, delaying gastric emptying, and/or reducing appetite in an animal or human.

As used herein, the term "polypeptide" refers to a polymer in which monomer amino acids ("amino acid residues") are joined together through peptide or disulfide bonds. It also refers to either a full-length naturally occurring amino acid sequence, to an analogue of a naturally occurring sequence, or to a fragment thereof between, for example, about 8 to about 500 amino acids in length. The polypeptides of the invention can be naturally occurring or synthetic. Unnatural amino acids, for example, beta-alanine, phenyl glycine and homoarginine, can be included within a polypeptide sequence. All of the amino acids of the polypeptides used in the present invention can be either the D- or L-optical isomer. Peptide nucleic acids (PNAs) are also included within the scope of the invention. A PNA is a DNA-mimic having a polypeptide-like inorganic backbone composed of, for example, N-(2-aminoethyl)glycine units, with an organic base (A, G, C, T or U) attached to the glycine nitrogen via a methylene carbonyl linker (Nielsen, P. et al., *Bioconjug. Chem.*, 5:3-7, 1994). Polypeptide active agents suitable for the methods and devices of the present invention can be, for example, from about 3 amino acids (aa) in length to about 200 aa in length; from about 8 aa to about 150 aa in length; from about 15 aa to about 100 aa in length; from about 25 aa to about 75 aa in length; from about 30 aa to about 50 aa in length; or from about 39 aa to about 50 aa in length. In some embodiments, the polypeptide is about 5 aa to about 20 aa in length, or about 5 aa to about 12 aa. In yet other embodiments, the polypeptide is about 30 aa to about 50 aa in length, or about 39 aa to about 50 aa in length. Suitable polypeptide active agents include those having a molecular weight in the range of about 500 Daltons to about 100,000 Daltons, and, in particular, to those having molecular weights in the range of about 500 Daltons to about 50,000 Daltons, about 500 Daltons to about 25,000 Daltons, and about 500 Daltons to about 10,000 Daltons, as well as those having molecule weights in the range of about 1,000 Daltons to about 8,000 Daltons, about 1,000 Daltons to about 6,000 Daltons, about 2,000 to about 5,000 Daltons, or about 3,000 Daltons to about 5,000 Daltons.

"Treatment" refers to the administration of medicine or the performance of medical procedures with respect to a patient, either for prophylaxis (prevention) or to cure the infirmity or malady in the instance where the patient is afflicted.

A "therapeutically effective amount" is an amount sufficient to decrease, prevent or ameliorate the symptoms associated with a medical condition.

Described herein are implantable delivery devices composed of homogenous porous hydrogels that are suited for delivery of polypeptides and their analogues, and methods of making the devices. The devices, when implanted into a subject, provide sustained delivery of polypeptide active agents to the subject.

Hydrogels allow for the diffusion of molecules in aqueous environments. It has been hypothesized that there are three classes of water in hydrogels, including, "Z" water, which is bound to the polymer matrix, "Y" water, which is partially affected by the polymer matrix, and bulk or "X" water, which is unaffected by the polymer matrix. This theory was expanded with the notion that the diffusion of hydrophilic solutes through hydrogel membranes depends on molecular size of the solute and water content of the hydrogel and that the permeation takes place via the bulk water (Refojo, M. and Leong, F., *J. Polymer Sci.: Polymer Symp.*, 66:227-237, 1979; Kim, S. et al., *ACS Symp. Ser.*, 127:347-359, 1980).

As described herein, the inclusion of certain liquid diffusion enhancers (which remain in liquid form following polymerization) in the mixture of polymerizable materials, permits the creation of a hydrogel having pores that are evenly dispersed and of a size to enhance diffusion of larger molecules through the network structure of the crosslinked polymer chains of the hydrogel. Additional characteristics and advantages of these liquid diffusion enhancers are described herein.

This invention may be especially useful in cases where the polypeptides are "pegylated," as this process significantly increases the original molecular weight by the polyethylene glycol (PEG) portion. As used herein, "pegylation" refers to the practice of adding PEG to a polypeptide active agent. This practice has been found to stabilize polypeptides by decreasing their recognition by the immune system and improving their half life.

One or more polypeptide active agents are embedded or substantially encased in a cartridge made of a biologically inert polymer matrix to form a delivery device suitable for sustained release of the polypeptide when implanted into a subject. The cartridges used in the devices are typically cylindrical hollow tubes made by extrusion, injection molding, reaction injection molding, compression molding, or spin-casting depending on the type of polymer used. Such cylindrical hollow tubes may have one or two open ends. Following molding or casting, the polypeptide active agent is introduced into the hollow core, or reservoir of the cartridge. Additional liquid material that is polymerizable may be introduced into the core opening and cured to seal the cartridge.

For those embodiments in which the cartridge is produced using a mold, one or more release agents are optionally present in the polymer matrix of the cartridge to aid in removal of the cartridge from the mold. The release agent is typically combined with the polymerizable material that ultimately forms the cartridge prior to introducing the polymerizable material into the mold.

Prior to implantation, the implantable formulations can be optionally hydrated or "primed" for a predetermined period of time. Priming can enable the active ingredient to begin to infiltrate and saturate the walls of the hydrogel and potentially begin to leach out of the hydrogel prior to implantation depending upon the amount of time the implant is primed. A primed implant begins to release active ingredient substantially upon implantation, and can result in a peak release of the drug shortly after implantation. In contrast, little to no priming can result in substantially no release of the active ingredient upon implantation for a period of time until the implant becomes hydrated and the active ingredient begins to be released. These priming characteristics depend on the specific formulations being used.

Depending upon the types of active ingredient, hydrophilic or hydrophobic, the appropriate conditioning and priming media are chosen. Water-based media are preferred for hydrophilic actives and oil-based media are preferred for hydrophobic actives. Alternatively, certain implants do not need to be primed prior to implantation. In some instances, priming improves delivery of the active agent in a controlled fashion, but in other instances, priming prior to implantation in a subject does not affect delivery in a way to justify the added time and hassle required for priming the implant.

The hydrating liquid useful in the practice of the invention is typically a liquid simulating the environment in which the active compound will be released, e.g., body fluid, sterile water, tear fluid, physiological saline solution, phosphate buffer solution and the like. While liquids other than water are useful as the hydrating liquid, the degree to which a hydrophilic membrane is hydrated is referred to as its "water content."

The priming and conditioning of the drug delivery devices involves the loading of the drug into the polymer that surrounds the reservoir, and thus prevent loss of the active before the actual use of the implant. The conditions used for the conditioning and priming step depend on the active agent, the temperature and the medium in which they are carried out. The conditions for the conditioning and priming can be the same in some instances.

The conditioning and priming step in the process of the preparation of the drug delivery devices is performed to obtain a determined rate of release of a specific drug. The conditioning and priming step of the implant containing a hydrophilic drug can be carried out in an aqueous medium, e.g., in a saline solution. For hydrophobic drugs, the medium can be a plasma-like medium, including, for example, cyclodextrin. The conditioning and priming steps are carried out by controlling three specific factors, namely the temperature, the medium and the period of time.

A person skilled in the art would understand that the conditioning and priming step of the drug delivery device is affected by the medium in which the device is placed.

The temperature used to condition and prime the drug delivery device can vary across a wide range of temperatures, but, in some embodiments, 37° C., is used.

The time period used for the conditioning and priming of the drug delivery devices can vary from about an hour, about 1 to about 12 hours, about 2 to about 24 hours, about a single day, or up to several weeks, e.g., 6 weeks, depending on the release rate desired for the specific implant or drug.

A person skilled in the art will understand the steps of conditioning and priming the implants, where appropriate or necessary, is to optimize the rate of release of the drug contained within the implant. As such, a shorter time period spent on the conditioning and the priming of a drug delivery device can result, for example, in a lower rate of release of the drug compared to a similar drug delivery device that has undergone a longer conditioning and priming step. Without priming, however, it was unexpectedly found that effective release occurred over a longer period of time (e.g., 28 weeks and beyond), and lower serum concentrations of the active ingredient were found to have ameliorative effects.

The temperature in the conditioning and priming step can also affect the rate of release in that a lower temperature results in a lower rate of release of the drug contained in the drug delivery device when compared to a similar drug delivery device that has undergone a treatment at a higher temperature. Similarly, in the case of aqueous solutions, e.g., saline solutions, the sodium chloride content of the solution determines the release rate for the drug delivery device. More specifically, a lower content of sodium chloride can result in a higher rate of release of drug when compared to a drug delivery device that has undergone a conditioning and priming step where the sodium chloride content was higher.

To identify the location of the implant, radiopaque material can be incorporated into the delivery device by inserting it into the reservoir or by making it into end plug to be used to seal the cartridge.

Methods for the preparation of the hydrogels are described in detail in U.S. Pat. No. 6,361,797, for example, which is incorporated by reference herein in its entirety. Materials that are utilized in the reaction mixture used to form the matrix, including the monomers, co-monomers, diffusion enhancers, and the like, are preferably biologically compatible and biologically inert, e.g., have no significant effect on animals or the human body. The materials for some embodiments have previously been approved for use in animals by the USDA and/or for use in humans by the FDA, or equivalent agencies. Such prior regulatory approval, however, is not a requirement. It is well within the skill of those in the art to select suitable materials.

Polymerizable material useful in the manufacture of the homogenous porous hydrogels of the devices include a wide variety of hydrophilic, ethylenically unsaturated compounds, in particular, hydrophilic monomers such as the monoester of an acrylic acid (e.g., methacrylic acid) with a polyhydroxy compound having an esterifiable hydroxyl group and at least one additional hydroxyl group such as the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the 2-alkenamides, e.g., acrylamide, methacrylamide, and the like; the N-alkyl and N,N'-dialkyl substituted acryl-amides and methacrylamides such as N-methylmethacrylamide, N,N'-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like. Other suitable monomers include those described in U.S. Pat. No. 4,303,066. In one desired embodiment, the co-monomers are a mixture formed of at least two of the above hydrophilic monomers. Alternatively, the co-monomers are a mixture formed of at least one hydrophilic monomer and at least one hydrophobic monomer.

In some embodiments, the hydrophilic monomer is 2-hydroxyethyl methacrylate (HEMA). Suitable co-monomers useful in the invention include HEMA and N,N'-dimethylacrylamide or HEMA and methacrylic acid. Still other suitable monomers and co-monomers can be readily selected from among those known in the art.

Useful crosslinking agents that can be included in the polymerizable reaction medium include, for example, the polyethylenically unsaturated compounds having at least two polymerizable ethylenic sites, such as the di-, tri- and tetra-ethylenically unsaturated compounds, in particular, the tri-unsaturated crosslinking agents with/without the di-unsaturated crosslinking compounds, for example, divinylbenzene, ethylene glycol dimethacrylate and diacrylate, propylene glycol dimethacrylate and diacrylate, and the di-, tri- and tetra-acrylate or methacrylate esters of the following polyols; triethanolamine, glycerol, pentaerythritol, 1,1,1,-trimethylolpropane; and others. Other suitable crosslinking agents may be readily selected by one of skill in the art.

Diffusion enhancers can be mixed with the polymerizable materials. Mixing can be done in a way to achieve uniform distribution and dispersion (e.g., by mixing, spinning, etc.) in the reaction medium, however the diffusion enhancers(s)but do not themselves polymerize. Rather, following the polymerization reaction, pores containing these diffusion enhancers are formed within the polymerized hydrogel material. Thus, the diffusion enhancers are liquids at room and/or body temperatures both prior to and following the polymerization reaction. These compounds include, for example, methyl alcohol, ethyl alcohol, propyl or isopropyl alcohol, allyl alcohol, tetrahydrofurfuryl alcohol, cyclohexyl alcohol, diethylene glycol, polyethylene glycols, glycerol, acetone, ethylene glycol monomethyl ether, ethylene glycol monoethyl ether, ethylene glycol monobutyl ether, glyceryl isopropylidene ether dioxane, tetrahydrofuran, ethyl acetate, dimethyl sulfoxide and water. Water soluble micronized solids can also be used for this purpose. Such water soluble micronized solids include, for example, any solid that will dissolve to leave pores within the polymerized hydrogel material, including, e.g., sugar, baking soda, and sodium chloride. Other diffusion enhancers can be selected according to known properties by one of skill in the art, particularly from among those compounds that are miscible with the starting monomers and are soluble in water.

Unlike formulations described by others, the diffusion enhancers described herein do not interfere with homogeneity during spin casting, and thus permit the formation of more homogenous hydrogels. These advantages are particularly apparent when spin or rotational casting is used to prepare the articles of the invention.

One or more release agents are optionally included in the polymerizable reaction medium. In general, release agents are compounds capable of allowing effective release of a molded article from a mold. For the devices of the present invention, the release agent is typically combined with the polymerizable reaction medium prior to introducing the polymerizable material to a mold.

Release agents suitable for use in the implantable devices are safe for introduction into a patient, do not adversely react with the polymer of the molded article, for example, by causing weakening of the structure of the article, and optionally protect the polymer cartridge from adverse effects of sterilization. Without being bound by theory, it is believed that higher molecular weight release agents provide improved release characteristics over those provided by lower molecular weight release agents. Release agents accordingly can have a molecular weight (MW) in excess of about 1000. In other embodiments, the release agents have a MW in excess of about 1200, from about 1000 to about 2000, or between about 1200 and about 1800.

Suitable release agents include non-ionic surfactants. In some embodiments, for example, the release agent is Vitamin E TPGS. Vitamin E TPGS is an abbreviation for D-α-tocopheryl (Vitamin E) polyethylene glycol 1000 succinate. Non-ionic surfactants release agents provide excellent release properties and are non-reactive with the molded article while providing a safety profile that is suitable for implants. These release agents additionally can act as antioxidants or free radical scavengers and, therefore, prevent or reduce adverse effects on the molded article associated with sterilization of the molded article, especially sterilization methods that can generate free radicals, including irradiation methods. In particular embodiments, the release agent dissolves in a desired monomer mixture. A hydrophilic monomer material, such as, for example combinations of HEMA, HPMA and HBMA, can be used in combination with an amphiphilic release agent, such as, for example, Vitamin E TPGS, during the molding process.

Non-ionic surfactants are known in the art, and may generally consist of a polyethylene glycol hydrophilic tail and a lipophilic head. For Vitamin E TPGS, for example, the lipophilic head is tocopherol succinate and for Triton X-100 it is an isooctylphenyl group. Non-ionic surfactants can be characterized by several parameters, such as, for example, hydrophilic-lipophilic balance (HLB), which relates the size of the polyethylene glycol tail to the lipophilic head; critical micelle concentration (CMC), which is the concentration of surfactant at which micelles form; and MW, which describes the size of the hydrophilic and lipophilic portions relative to other surfactants with similar properties. Additionally, CMC is an indication of the surface activity of the surfactant, and a low CMC is indicative of a more stable micelle because of stronger binding forces. The Table below lists several surfactants and their physical properties.

TABLE 1

Surfactants

| Name | ~MW | HLB | CMC (mM) |
|---|---|---|---|
| Triton X-100 | 625 | 13.5 | 0.2-0.9 |
| Vitamin E TPGS | 1513 | 13 | 0.1 |
| Triton X-114 | 537 | 12.4 | 0.2 |
| Brij 35 | 1200 | 16.9 | 0.05-0.1 |
| Tween 20 | 1228 | 16.7 | 0.06 |
| Tween 80 | 1310 | 15 | 0.012 |
| Sucrose monolaurate | 525 | ~8 | 0.2 |

Additional release agents for use in combination with the implantable devices include, but are not limited to, polyoxyethylene(2) stearyl ether, sorbitan monolaurate, polyoxyethylene(5)nonylphenyl ether, polyoxyethylene(20)sorbitan trioleate, polyoxyethylene(10)isooctylphenyl ether, and the like, or combinations of these release agents.

In certain embodiments, the release agent is a polyoxyethylene ester of fatty acids or other hydrophobic compounds. These compounds are known in the art and include a polyoxyethylene tail and a saturated or unsaturated hydrophobic head. The hydrophobic moiety of various embodiments can include any aromatic group containing moiety or polycyclic aromatic moieties such as, for example, a phenol, a catechol, a resorcinol, a hydroquinone, a tocopherol, Vitamin E, and the like and can be isoprenoid or non-isoprenoid. The side chains associated with these aromatic moieties can be of any length and can additionally include any number of double bonds and/or substitutions. Non-ionic surfactants, for example, can include, but are not limited to, naturally occurring or commercially manufactured tocopherols including any isoform, racemate, or chemically modified derivative, such as, Vitamin E TPGS. Tocopherols can also include oxidation products of tocopherols, such as the oxidation products of α-tocopherol, tocopherol quinones, tocopherol hydroquinones, epoxytocopherols, and nitrotocopherols.

A polymerizable mixture is formed, for example, by mixing co-monomers with a crosslinker and a diffusion enhancer, e.g., about 50% to about 95%, about 60% to about 90%, or about 75% to about 85%, by weight, of the polymerizable monomers can be included in the mixture. Generally, the crosslinker is added in an amount in the range of about 0.1% to about 5%, about 0.5% to about 3%, and about 1%, by weight, of the mixture. The diffusion enhancers are generally included in an amount of about 1% to about 50%, about 5% to about 40%, about 10% to about 30%, or about 20%, by weight, of the mixture.

The polymerizable mixture can be polymerized to produce a polymer or copolymer matrix. The polymerization reaction can be carried out in bulk or with an inert solvent. Suitable solvents include, but are not limited to, water; organic solvents such as water-soluble lower aliphatic monohydric alcohols as well as polyhydric alcohols, e.g., glycol, glycerine, dioxane, etc., and mixtures thereof.

Compounds useful in the catalysis of the polymerizable ethylenically unsaturated compounds include the free radical compounds and/or initiators of the type commonly used in vinyl polymerization such as the organic peroxides, percarbonates, hydrogen peroxides, and alkali metal sulfates. Illustrative examples include, but are not limited to, cumene hydroperoxide, t-butyl hydroperoxide, benzoyl peroxide, bis(4-t-butylcyclohexyl)peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. In one embodiment, the catalyst is effective at a moderately low temperature such as, for example, at about 20-80° C. (e.g., tert-butyl peroctoate, benzoyl peroxide, and di(secbutyl)peroxydicarbonate).

A conventional redox polymerization catalyst can also be employed. Polymerization of the ethylenic compounds can be effected, for example, using radiation, e.g., ultraviolet, X-ray, gamma radiation, microwave or other known forms of radiation. An example of a catalyst for ultraviolet cure is benzoin methyl ether. Catalysts and/or initiators and/or radiation are employed in a catalytically effective amount to optimize the polymerization reaction. The advantage of redox initiation is that the reaction occurs at reasonable rates at low temperatures, e.g., 0° C. to 50° C., and can be effected in the presence of water. A large number of reductant-oxidant pairs producing free radicals is known in the art. Examples include sodium bisulfate and ammonium persulfate, sodium thiosulfate and potassium persulfate, and the like. Catalysts and/or initiators and/or radiation are employed in a catalytically effective amount to optimize the polymerization reaction.

The polymerization reaction can be conducted in a mold or polymerization column to form a cartridge that is used to construct an implantable device. Cartridges can be prepared from the polymerizable mixture using any method known in the art, such as, for example, extrusion, injection molding, reaction injection molding, compression molding or spin-casting.

To form a cartridge, the monomer(s), or polymerizable material prepared as described above is introduced to a mold or polymerization column. The molds and polymerization columns described herein have interior surfaces that are cylindrical, such that cross-sectional areas of the interior of the column are circular in shape and about equal in diameter and smooth. Molds and polymerization columns of various embodiments can be made of any suitable material, such as, for example, plastics, including, but not limited to, polyethylene, polypropylene, and polystyrene; metal; glass; and the like. In some embodiments, the column can be fabricated from a material that allows electromagnetic radiation to pass into the polymerization zone of the column, and in certain embodiments, glass, such as Pyrex™, is used to make the mold or polymerization column.

In some embodiments, cartridges are made by centrifugally-casting or spin-casting. In some of these embodiments, the cartridge is prepared by preparing a polymerization column or mold of appropriate size with one extremity of the column being closed and the other extremity being open-ended and adapting the polymerization column or mold for rotation about its longitudinal axis; introducing a monomer to the column or mold; rotating the column or mold about its longitudinal axis and maintaining it substantially parallel to the ground at a speed sufficient to displace the monomer radially outward along the interior surfaces of the column or mold such that the monomer assumes a cylindrical configuration with a core; polymerizing the monomer to convert it to a solid molded article having a concentric cylindrical core; and recovering the article, or reservoir cartridge. The speed at which the mold or polymerization column is rotated can vary, depending upon the size of the cartridge being made, the type of polymerizable material being used, and the effectiveness of the release agent. For example in some embodiments, the rotational speed may be from less than about 1000 rpm to greater than 6000 rpm, and in certain embodiments, the rotational speed may be about 2150 rpm.

The polymerizable material in the cartridge can also be optionally cured. Curing can be carried out any one of a number of methods known in the art and for any period of time depending on the type of polymerizable material used and the size of the cartridge being prepared. For example, when the polymerizable material has achieved the predetermined shape, the mold or polymerization column can be irradiated with ultraviolet light for a period of time, such as, for example, from about 1 to about 10 minutes, to initiate polymerization of the polymerizable material. The cartridge can then undergo thermal curing and annealing. In some embodiments, the cartridge is thermally cured for about 60 minutes at a temperature up to about 100° C. followed by post-curing for about 30 minutes at a temperature up to about 120° C. and annealing for about 30 minutes at about up to 130° C., followed by gradual cooling to ambient temperature (about 25° C.). The cured cartridge is removed from the mold or polymerization column, washed to remove excess release agent and/or to extract pore formers, and polished to achieve a smooth, unscored surface. After shaping and polishing the closed end of the cartridge to a oval-like cylindrical profile, there is obtained small, cylindrically shaped objects having smooth, unscored cylindrical surfaces. Typical dimensions of the cartridges are as follows: internal radius 0.98 mm; external radius 1.3 mm; length 25 mm.

In some embodiments in which a cylindrical cartridge is used to form the implantable device, the length of the hydrated cartridge can be from about 5 mm to about 60 mm, and the external diameter may be from about 1.5 mm to about 5 mm. While the release agents can be used in any size implant, in some embodiments, the release agents are used in the preparation of larger implant devices. The length of a hydrated cartridge prepared using a non-ionic surfactant release agent can be from about 40 to about 60 mm, for example, and the external diameter can be from about 3 to about 5 mm. In some embodiments, the length of a hydrated cartridge is 45 to 60 mm, and the external diameter is from 3.5 to 4.8 mm. Without wishing to be bound by theory, non-ionic surfactant release agents can overcome the surface tension in molds used during preparation of cartridges while allowing the cartridge to be readily released from the mold. In certain embodiments, a larger cartridge can be used for large animals or livestock, such as, for example, sheep, cows, goats, cattle, and the like because larger animals can tolerate implantation of larger drug delivery devices.

The external surface area of the implant, e.g., the external surface area of the polymer cartridge or hollow tube, can vary. In some embodiments, the surface area of the polymer cartridge can have a surface area of from about 350 mm$^2$ to about 1500 mm$^2$. Hydrated implants and xerogel (e.g., non-hydrated, or dry) implants have different dimensions and, therefore, different surface areas. In some embodiments, the release agents are used in the preparation of larger implant devices. A xerogel, non-hydrated, or dry implant, for example can have a surface area of about 350 mm$^2$ or greater. Alternatively, a xerogel, non-hydrated, or dry implant can have a surface area of from about 350 mm$^2$ to about 1500 mm$^2$, or from about 350 mm$^2$ to about 600 mm$^2$. The dry implant, for example, can have a surface area from 378 mm$^2$ to 660 mm$^2$. Additionally, a hydrated implant can have a surface area of about 500 mm$^2$ or greater. The hydrated implant alternatively can have a surface area of from about 600 mm$^2$ to about 1500 mm$^2$, or from about 600 mm$^2$ to about 800 mm$^2$. As used herein, the term "hydrated implant" refers to implants having a water content of 5% (wt), or greater, and are thus soft and flexible. As used herein, "dry implant" refers to implants that are rigid and inflexible, having a water content less than 5% (wt), in some embodiments, and less than 1% (wt), in other embodiments.

The implantable devices can be inserted subcutaneously in a human or other animal by any suitable means known in the art, e.g., by perforation (for subcutaneous implantation) or by other means, e.g., open surgery (U.S. Pat. No. 5,266,325, which discloses examples of methods and devices that can be used to implant the devices; the entire contents of U.S. Pat. No. 5,266,325 are herein incorporated by reference). The implantable device can be inserted subcutaneously in the human or animal by perforation, for example. In addition, more than one device can be implanted into the human or animal at the same time, e.g., substantially simultaneously, so that multiple devices are present as implants in the human or animal. Thus, in some embodiments, at least one device is implanted into the human or animal. Alternatively, multiple devices can be implanted sequentially, so that only one device is present in the human or animal at any one time. Such devices are characterized by a length of 10-50 mm, or less (e.g., 6-9 mm), an external diameter of 2-5 mm, or less (e.g., 1.5-1.9 mm). The dimensions of the cartridge can vary outside of the limits stated above depending, in particular, on the medical application involved. Animals such as sheep, cows, goats, cattle, and large animals, in general, can tolerate implantation by perforation of the larger-dimensional implantable devices.

Smooth, unscored cylindrically shaped objects of various lengths, e.g., up to 25 cm and longer, can also be prepared in accordance with the teachings herein. Such objects, in a hydrated state or plasticized with a non-toxic, biocompatible material, can be formed into desired shapes, e.g., a ring shape, for use as pessaries, surgical implants, etc. Yet other devices can be prepared using techniques known to those of skill in the art.

The implantable devices are prepared by introducing a pre-determined amount of one or more polypeptide active agents, optionally combined with a pharmaceutically acceptable carrier, into the reservoir, or core, of a cartridge obtained by the methods described above.

Polypeptides suitable for use as active agents in the implantable devices include, but are not limited to, growth factors, interferons, interleukins, granulocyte macrophage colony stimulating factor (GM-CSF), neurotrophic factors and the like. Additional examples of polypeptides include exendins (including, e.g., exendin-4, exenatide, and liraglutide); amylin analogues (e.g., pramlintide); corticotropin releasing factor (CFR) and CFR receptor antagonists (including, e.g., astressin); β-endorphins (including, e.g., β-lipotropin) and γ-endorphins; endostatins; endostatins; galanins; gastric inhibitory peptide; ghrelins (e.g., ghrelin and obestatin); glucagon; incretins, including glucagon-like polypeptides; pancreatic polypeptides; polypeptides produced in the ileum or colon (including, e.g., $PYY_{3-36}$); adipokines (including, e.g., omentin); leptin; oxyntomodulin; pituitary adenylate cyclase activating peptides (PACAP); somatostatin analogues or mimics such as octreotide; polypeptides that favor energy expenditure (including, e.g., melanocortin, α-MSH, and polypeptides that signal through the POMC (pro-opiomelanocortin) and CART (cocaine- and amphetamine-regulated transcript) pathways); and analogues and fragments thereof.

Further examples of suitable polypeptide active agents include those having antiretroviral activity, e.g., HIV fusion inhibitors such as enfuvirtide (marketed as Fuzeon® by Roche, and disclosed in U.S. Pat. No. 5,464,933, the entire contents of which are herein incorporated by reference (Tyr-Thr-Ser-Leu-Ile-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Ala-Ser-Leu-Trp-Asn-Trp-Phe; SEQ ID NO:1)), and analogues and fragments thereof. Polypeptides also considered suitable for use in the implantable devices include growth hormone and growth hormone releasing factors (GHRF), growth hormone releasing peptides (GHRPs), and analogues and fragments thereof. Examples of growth hormone releasing peptides (GHRPs) include, e.g., GHRP-6, and GHRP-2 (e.g., Pralmorelin (under development by Kaken Pharmaceuticals), which is disclosed in U.S. Pat. No. 7,008,927).

Additional examples of polypeptides that can be used in the implantable devices include calcitonin and calcitonin gene related polypeptides, as well as parathyroid hormone (PTH) (including, e.g., teriparatide (marketed as Forteo® by Eli Lilly and Co., and disclosed in U.S. Pat. No. 6,770,623, the entire contents of which are herein incorporated by reference (Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe; SEQ ID NO:2)), and analogues and fragments thereof.

For yet additional specific examples of polypeptides suitable for use in the devices and methods described herein, see American Peptide Company, Inc., Peptide catalog 2006-2007, in particular, pages 119, 171, 175, 207, 211, 217, 219, 227, 315, 317, and 329, the contents of which are herein incorporated by reference. See also the following U.S. patents and published patent applications: U.S. Patent Publication Nos. 20050287320; 20070010656; 20060293232; 20060233747; 20060148713; 20060122106; 20060035836;

20060030528; 20040002454; 20030036504; and 20020141985; and U.S. Pat. Nos. 7,271,238; 7,259,136; 7,220,721; 7,153,825; 7,118,737; 7,115,569; 7,105,489; 7,101,853; 7,056,887; 7,008,927; 6,969,480; 6,942,264; 6,872,700; 6,770,623; 6,602,694; 6,579,851; 6,417,164; 6,143,718; 6,087,334; 5,686,411; and 5,464,933. The entire contents of each of these U.S. patents and published patent applications is herein incorporated by reference in its entirety.

In some embodiments, the polypeptide active agent is an incretin mimetic, e.g., a GLP-1 analogue such as an exendin (e.g., exendin-4, or exenatide (disclosed in U.S. Pat. No. 6,872,700, the entire contents of which are herein incorporated by reference (His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser; SEQ ID NO:3), and marketed as Byetta® by Amylin Pharmaceuticals, Inc.)), or a fragment or analogue thereof. For example, in some embodiments, the polypeptide active agent is the GLP-1 analogue Liraqlutide (having the chemical structure Arg(34)Lys(26)-(N-epsilon-(gamma-Glu (N-alpha-hexadecanoyl))-GLP-1(7-37) (e.g., as disclosed in WO 2007/028394).

In other embodiments, the polypeptide active agent is an amylin mimetic, e.g., pramlintide (disclosed in U.S. Pat. No. 5,686,411, the entire contents of which are herein incorporated by reference (Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr; SEQ ID NO:4); pramlintide acetate in an injectable form is marketed as Symlin® by Amylin Pharmaceuticals, Inc.), or a fragment or analogue thereof.

The polypeptide active agent can be present in free form or in the form of a pharmaceutically acceptable salt, such as, for example, an acetate salt, pamoate salt, gluconate salt, lactate salt, or hydrochloride salt.

In various embodiments, the polypeptide active agents are combined with one or more pharmaceutically acceptable carriers to produce solutions, emulsions, suspensions, and the like that are suitable for use in the implantable devices. Methods of formulating the polypeptide active agent and the pharmaceutically acceptable carrier are known to those of skill in the art, and various pharmacologic references can be consulted for guidance. See, for example, Remington's Pharmaceutical Sciences, Osol, A., ed., Mack Publishing Company, Easton, Pa. (1980).

Suitable pharmaceutically acceptable carriers may be in the form of suspending media, solvents, aqueous systems, and solid substrates or matrices, as described in U.S. Pat. No. 6,361,797. Suspending media and solvents useful as the carrier include, for example, oils such as silicone oil (particularly medical grade), corn oil, castor oil, peanut oil and sesame oil; condensation products of castor oil and ethylene oxide containing about 30 to 35 moles of ethylene oxide per mole of castor oil; liquid glyceryl triesters of a lower molecular weight fatty acid; lower alkanols; glycols; and polyalkylene glycols.

Aqueous systems include, for example, sterile water, saline, dextrose, dextrose in water or saline, and the like. The presence of electrolytes in the aqueous systems may tend to lower the solubility of the polypeptide active agent in them.

Solid substrates or matrices include, for example, starch, gelatin, sugars (e.g., glucose), natural gums (e.g., acacia, sodium alginate, carboxymethyl cellulose, hydroxypropylcellulose), and the like. The carrier can also contain adjuvants or additional excipients such as preserving, stabilizing, wetting and emulsifying agents, diluents and the like, including, for example, magnesium stearate, stearic acid, and the like. Additional examples of adjuvants and excipients are known to those of skill in the art.

The polypeptide active agent can be combined with a pharmaceutically acceptable carrier that is a solid substrate or matrix (e.g., hydroxypropylcellulose), and is optionally combined with one or more additional excipients, to form a solid formulation comprising the polypeptide. In those embodiments in which the polypeptide is in a solid formulation, the polypeptide is also in solid form, e.g., a powder. Solid forms of polypeptides can be obtained using methods known in the art, including, but not limited to, precipitation, crystallization, spray drying, air drying, freeze drying (lyophilization), vacuum drying, and open drying. For example, in some embodiments, solid polypeptide is prepared by lyophilizing an aqueous solution of the polypeptide. The powdered polypeptide can be in a granular or particulate form. If the polypeptide has an amorphous structure or has a particle size that is heterogeneous and poorly defined, it can be further processed to produce a particulate, granular powder using any suitable method known in the art, including, but not limited to, milling the solid polypeptide (see, e.g., U.S. Pat. Appl. Publ. No. 2006/0067911), or spray drying a solution of the solid polypeptide to produce a granular powder.

In some embodiments, the powdered polypeptides are in a granular or particulate form having particles of well-defined size (e.g., particles falling within a defined size range). Methods for reduction of particle size are known in the art and include, for example, milling (using, e.g., ball, rod, hammer, colloid or fluid-energy mills). The particle size can be controlled using standard techniques well known to those of ordinary skill in the art. Suitable particle sizes are generally about 500 microns or less in diameter. The polypeptide particles can range in size from about 10 microns to about 500 microns. It will be appreciated that the particle sizes specified above are exemplary and that particle sizes that vary slightly from those mentioned above, e.g., ±20%, such as ±10% or ±5%, are encompassed by the use of the term "about."

The implantable devices are formed by introducing into the core of the device, for example, into the cartridge, one or more polypeptide active agents, optionally combined with one or more carriers to form a polypeptide formulation, and then partially filling the core. In some embodiments, after the core has been partially filled, a layer of an inert material, such as Teflon tape, can be placed on top of the active agent, and the void in the core above the covering can be sealed to prevent leakage into or out of the cartridge. The seal can be formed by filling the void with a polymerizable material, such as a polymerizable material used to make the cartridge, and polymerizing the polymerizable material to form a plug that seals the opening of the cartridge. In some embodiments, the polymerizable material used to form the plug can be the liquid polymerizable material used to make the cartridge and may not have an equilibrium water content value exceeding the equilibrium water content value of the hydrophilic cartridge, upon maximum hydration. In other embodiments, the polymerizable material can be of similar composition but with a higher hydrophilicity than the liquid polymerizable material employed in the fabrication of the cartridge.

In some embodiments, a plug for a cartridge having a core filled with polypeptide active agent and covered with teflon tape, can be made by first cleaning and slightly increasing the internal surface area of the core above the polypeptide agent by careful reaming the open end of the cartridge with an appropriate reamer. The reamed surface area can then be cleaned with a sufficient amount of a mono or polyhydric alcohol, such as, for example, ethanol, causing a slight swelling of the surface of the cartridge. Using a fine needle syringe, a small amount of the liquid polymerizable material can be injected into the cartridge filling the core to the top. The polymerizable material can then be polymerized by positioning the cartridge so that its longitudinal axis is perpendicular to the ground, rotating the cartridge on using for example, a lathe at a relatively low speed, such as, about 100 rpm to about 200 rpm, and exposing the cartridge to ultraviolet light for several minutes, for example, 5-10 minutes. In the event the active agent is sensitive to ultraviolet light, a shield such as, for example, aluminum foil can be used to shield the active compound from the ultraviolet light. In general, the curing of the plug should take place at a temperature that is not detrimental to the drug, for example, ambient temperature. Without wishing to be bound by theory, reaming and cleaning the open end of the cartridge promotes the penetration of the polymerizable hydrophilic material into the treated surface.

The filled and sealed cartridges can be sterilized by any sterilization technique known in the art, depending on the material used to make the cartridge and the active agent to be delivered. For example, suitable sterilization techniques include, but not be limited to, heat sterilization, radiation sterilization, such as cobalt 60 irradiation, gamma radiation, or electron beams, ethylene oxide sterilization, and the like. In certain embodiments, agents affixed to the cartridge can act as an antioxidant or free radical scavenger during sterilization to reduce or eliminate the adverse affects of free radicals formed during sterilization by, for example, irradiation.

The implantable devices can also be readily adapted to delivery of combinations of one or more of the various types of polypeptides described above.

The amount of polypeptide active agent employed in the implantable devices depends not only on the desired daily dose but also on the number of days that dose level is to be maintained. While this amount can be calculated empirically, the actual dose delivered is also a function of any interaction with materials and the carrier, if employed in the device. The polypeptide compositions are present in the sustained release compositions in varying amounts, depending upon the effect desired.

The polymeric matrix of the xerogel implantable device can be hydrated prior to implantation to form the hydrogel, and the device implanted into a subject in a hydrated state. Alternatively, the implant may self-hydrate upon implantation as a dry implant, and thus, no hydration of the implant prior to implantation is necessary.

To form a hydrogel, the polymer matrix must be hydrated, typically by exposure to an aqueous solution or to aqueous media. Upon exposure to aqueous media, the xerogel absorbs the aqueous fluid to become a hydrogel containing pores which are relatively evenly dispersed throughout the hydrogel matrix. Suitably, the pores formed in the hydrogel range in size from 10 Angstroms ($1 \times 10^{-9}$ m) to several microns. Other suitable ranges include from 50 Angstroms to 0.1 microns and from 0.1 microns to 1 micron. When the molecule for delivery is a macromolecule, the pore size is suitably over 50 Angstroms. As described herein, the pores contain diffusion enhancers.

The hydrating liquid used to prepare the hydrogel is typically a liquid simulating the environment in which the polypeptide active agent will be released, e.g., body fluid, sterile water, tear fluid, physiological saline solution, phosphate buffer solution, and the like. While liquids other than water are useful as the hydrating liquid, the degree to which a hydrophilic membrane is hydrated is referred to as its "water content."

The hydrogel does not dissolve upon exposure to water, but permits the imbibing of water. When a hydrogel attains it maximum level of hydration, the water content of the hydrogel is referred to as "equilibrium water content" (EWC). The percent water content of the hydrogel (any state of hydration) is determined as described in U.S. Pat. No. 6,361,797.

A hydrogel described herein can have an EWC value in the range of from about 20% to about 90%, about 35% to about 85%, or about 50% to about 80%, as desired. Advantageously, the hydrogels of the invention have an increased EWC value, as compared to the equivalent hydrogels without diffusion enhancers. Such improvements in EWC value correspond with an increase in release rate.

It is the ability of the hydrogel to swell with water, and thus, increase the area between the cross-links, which permits the passage of the polypeptide active agents. By controlling the level of hydration, it is possible to control the rate of passage of these active agents through the hydrogel matrix into the surrounding environment, e.g., the body. The use of the diffusion enhancers as described herein facilitates passage of the polypeptide active agents. More particularly, during hydration of the hydrogel, the diffusion enhancers leach out of the hydrogel into the surrounding environment, thus permitting the pores to fill with water from the surrounding environment. The presence of the diffusion enhancers as described herein permits the formation of pores, which are larger than those found in their absence. Diffusion enhancers include, but are not limited to, saline, isotonic water, and phosphate buffered saline. These pores provide larger spaces that permit the passage of macromolecular active agents into the surrounding environment.

The hydrogels can be selected to be non-toxic, and once hydrated, to contain no residual monomers or extractables. Further, the hydrogels are characterized by low reactivity, and are sufficiently flexible that they mimic the surrounding tissue. Thus, these hydrogels are well suited for use in the animal, particularly, mammalian and more particularly, human body.

Upon implantation, the devices provide sustained release of the polypeptide active agent drugs over extended periods of time. This time period can range from several days to a few years, for example, from one week to three years depending on the desired administration regimen. The release time can be about a week to about 18 months or longer, it being understood that this time factor is variable depending on the rate-releasing membrane of choice, its interconnecting pore structure, the active compound of choice, the solubility of the active compound in the liquid medium, and other considerations known to those skilled in the art. In some embodiments, the implantable devices provide sustained release of the polypeptide active agent over an extended period of time that lasts at least one month. In other embodiments, sustained release of the polypeptide is provided over an extended period of time lasts at least two months, at least three months or at least six months. In yet other embodiments, the extended period of time of release of the polypeptide lasts at least one year.

In some embodiments, the implantable devices described above can be used in a method of delivering a sustained release of a polypeptide to a subject, allowing the device to release on a daily basis an effective amount of the polypeptide over a defined period, e.g., a period of at least about two months, at least about three months, or at least about six months. For example, in some embodiments, the implantable device can be used in a method of delivering a sustained release of a polypeptide to a subject in need thereof, the method comprising inserting beneath a subject's skin an implantable device comprising a homogeneous copolymer matrix, including a release agent having a molecular weight (MW) of at least about 1000, and a solid formulation comprising a polypeptide, which is substantially encased within the matrix; and allowing the device to release on a daily basis an effective amount of the polypeptide over a period of at least about two months.

Methods for determining the release profile (e.g., delay time, release rate and duration) of a macromolecular composition from the implantable devices are well known, and include use of the Fick's First Law of Diffusion. See, e.g., U.S. Pat. No. 5,266,325, which is herein incorporated by reference.

In some embodiments, the implantable devices provide delayed/sustained release or immediate/sustained release of one or more polypeptides to an animal. "Delayed/sustained release" is defined as delaying the release of the polypeptide active agent until after placement in a delivery environment, followed by a sustained, preferably zero-order, release of the polypeptide at a later time. "Immediate/sustained release" is defined as the commencement of the release of the polypeptide active agent immediately or soon thereafter after placement in a delivery environment, followed by sustained release of the polypeptide. Other applications of the present invention include controlled delivery in industrial, agricultural and domestic settings.

The implantable devices of the present invention are designed to provide sustained release of polypeptide active agents and can be used in methods of treating various conditions or disorders in humans and animals depending upon the particular polypeptide active agent employed in the implantable device and the disease, disorder or condition against which the polypeptide is known to be effective.

For example, in some embodiments of the present invention, the polypeptide active agent is a GLP-1 analogue (e.g., exenatide or liraglutide) that exhibits glucoregulatory effects such as enhancing glucose-dependent insulin secretion by pancreatic beta-cells, lowering blood glucose levels, improving glycemic control, suppressing pancreatic glucagon release, delaying or slowing gastric emptying, and/or reducing appetite in an animal or human, effects all relevant to the treatment of diabetes.

Accordingly, the implantable devices described above can be used in a method of treating diabetes in a human or animal. In some embodiments, the method of treating diabetes in an animal comprises administering a GLP-1 analogue in an implantable device described above that provides sustained release of effective therapeutic amounts of the GLP-1 analogue to the human or animal over an extended period of time.

In some embodiments, the implantable devices can be used in a method of treating a subject suffering from a type of diabetes, comprising inserting beneath a diabetic subject's skin an implantable device comprising a homogeneous copolymer matrix, including a release agent having a molecular weight (MW) of at least about 1000, and a solid formulation comprising a GLP-1 analogue polypeptide (e.g., exenatide, liraglutide, and analogues thereof), which is substantially encased within the matrix; and allowing the device to release on a daily basis an effective amount of the polypeptide over a period of time, e.g., at least about two months, at least about three months, or at least about six months.

In some preferred embodiments, the implantable devices are used to administer a polypeptide in a method of treating type 2 diabetes.

The implantable devices described above can also be used in other methods relating to the other glucoregulatory effects of the GLP-1 analogue, e.g., in a method of enhancing glucose-dependent insulin secretion in an animal or human, lowering blood glucose levels in an animal or human, improving glycemic control in an animal or human, suppressing pancreatic glucagon release in an animal or human, slowing gastric emptying in an animal or human, reducing appetite in an animal or human, and treating obesity in an animal or human. Accordingly, the implantable devices can also be used, for example, in a method of treating hyperglycemia, or of treating insulin resistance, or treating metabolic syndrome, in a human or animal, the method comprising administering a polypeptide in a hydrogel implantable device that provides sustained release of effective therapeutic amounts of the polypeptide to the human or animal over an extended period of time.

In some embodiments, one of the implantable devices can be used in a method of treating a subject in need of glycemic control, the method comprising inserting beneath a hypoglycemic or hyperglycemic subject's skin an implantable device comprising a homogeneous copolymer matrix, and a solid formulation comprising a GLP-1 analogue polypeptide (e.g., exenatide, liraglutide, and analogues thereof), which is substantially encased within the matrix; and allowing the device to release on a daily basis an effective amount of the polypeptide over a period of time, e.g., over a period of at least about two months, at least about three months, or at least about six months.

Embodiments directed to a method of treating diabetes (e.g., to a method lowering blood glucose levels, or to a method of improving glycemic control) by administering a GLP-1 analogue such as, for example, exenatide or liraglutide using an implantable device described above, the GLP-1 analogue is administered in an effective daily dose of about 10 µg to about 100 µg, or preferably about 10 µg to about 50 µg (e.g., the implantable device provides sustained release of the GLP-1 analogue at a range of about 10 µg to about 100 µg GLP-1 analogue each day, preferably about 10 µg to about 50 µg per day).

In those embodiments directed to methods of treating certain conditions or disorders by administering a polypeptide using an implantable device described above, the polypeptide can be administered in combination with one or more other treatments or other medications that are designed to treat the same condition or disorder. The other treatment or medication can be administered by a route and in an amount commonly used, and can be administered concurrently or sequentially with the polypeptide. The other medication or treatment can also be administered prior to administration of the polypeptide.

In those embodiments in which the other treatment or medication is administered concurrently with the polypeptide, the other treatment or medication can be administered using the same route of administration as the polypeptide or using a different route of administration (e.g., including oral, parenteral (e.g., intramuscular, intraperitoneal, intravenous, intracisternal injection or infusion, subcutaneous injection, or implant), by inhalation spray, or by nasal, vaginal, rectal, sublingual, or topical routes of administration). The other treatment or medication can also be formulated together with the polypeptide, e.g., in the same implantable device, or formulated separately using any suitable dosage unit formulation known in the art.

Some embodiments are directed to a method of treating type 2 diabetes (e.g., to a method lowering blood glucose levels, or to a method of improving glycemic control) by administering a GLP-1 analogue such as exenatide or liraglutide using an implantable device described above. In some of these embodiments, the GLP-1 analogue can be administered in conjunction with another medication used to treat diabetes, such as pioglitazone, metformin, a sufonylurea, and/or insulin administered by routes and in amounts commonly used and known to the skilled clinician. For example, in some embodiments directed to a method of treating diabetes (e.g., directed to a method of improving glycemic control), a subject is administered the GLP-1 analogue exenatide using one of the sustained-delivery implantable devices of the invention, while at the same time receiving daily oral administration of metformin (e.g., in the form of a 500 mg oral tablet of metformin hydrochloride).

In other embodiments, e.g., in those embodiments directed to a method of treating obesity using an implantable device described above (for example, by administering an amylin mimetic such as pramlintide), the polypeptide administered using the implant (e.g., the amylin mimetic) can be administered in conjunction with one or more other agents designed to treat obesity, such as, for example, an oral formulation of sibutramine (e.g., a 5, 10 or 15 mg capsule of sibutramine hydrochloride, administered daily), a parenteral formulation of leptin (e.g., an injectable formulation), an oral formulation of orlistat (e.g., a 120 mg capsule of orlistat (tetrahydrolipstatin), marketed as Xenical® by Hoffmann-La Roche Inc.), an oral formulation of phentermine, an oral formulation of bupropion (e.g., Wellbutrin SR, marketed by GlaxoSmithKlein), or an oral formulation of rimonabant (marketed by Sanofi-Aventis in Europe under the name Acomplia).

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXEMPLIFICATION

Example 1

A monomeric mixture comprised of 94.5% 2-HEMA, 5% propylene glycol and 0.5% ethylene glycol dimethacrylate (EGDMA) was prepared. 2-HEMA was previously purified by vacuum distillation. To the resulting mixture, 0.2% benzoin methyl ether was added and dissolved.

An implant cartridge was initially prepared as described in U.S. Pat. No. 5,266,325. More particularly, the mixture was deoxygenated by bubbling nitrogen through it for 10 minutes. To avoid premature polymerization the mixture was shielded from light. One end of a polypropylene tube (65 mm in length and di of 2.5 mm) was plugged with a silicone sealant; the other end of the tube was sealed with a plug made by injecting a small amount of the above mixture, which was cured under a UV lamp for 5 minutes. Using a syringe filled with the mixture, the silicone plug was punctured and the tube was filled with the mixture to a height of about 10 mm from the top. The tube was inserted in a lathe collet and spun (spinning axis parallel to the ground) at about 2200 rpm. The centrifugal force created by the spinning tube caused the radially outward displacement of the mixture to assume a predetermined hollow cylindrical liquid configuration (a hollow tube of polymerizable liquid mixture). The spinning tube was then exposed to UV light for 7 minutes to polymerize the "liquid tube" to a solid hydrophilic tube (cartridge). The cartridge within the polypropylene tube was post-cured for 14 hours at 65° C., followed with an additional 40 minutes at 105° C., and annealed at 116° C. for 40 minutes, and then slowly cooled to 22° C.

The cartridge was ejected from the tube, inspected for defects, and cut to a length of 30 mm. There was obtained a precisely dimensional plastic cartridge fabricated of crosslinked homogeneous 94.5% HEMA/5% polypropylene glycol/0.5% EDGMA polymer characterized by recurring hydrophilic units. The weight of the cartridge was recorded.

This cartridge is available for filling with a polypeptide active agent by tightly packing it to a 20 mm height. The filled cartridge is weighed again to determine the weight of active agent. The empty space of the cartridge is filled with the aforesaid monomeric mixture. Part of the cartridge containing the active agent is covered with aluminum foil. The cartridge is then placed in the lathe and spun slowly (spinning axis of cartridge parallel to ground) under a UV lamp for 5 minutes to effect polymerization of the mixture. Post-curing of the polymer plug was effected by maintaining the cartridge at 50° C. for 18 hours. The end product is an implantable device.

Example 2

A monomeric mixture comprised of 92.5% 2-HEMA, 2% methacrylic acid, 5% polyethylene glycol 200 and 0.5% ethylene glycol dimethacrylate was prepared and processed as in Example 1.

Example 3

A monomeric mixture comprised of 74.5% 2-HEMA, 20% N,N'-dimethylacrylamide (N,N'-DMA), 5% isopropyl alcohol and 0.5% ethylene glycol dimethacrylate was prepared and processed as in Example 1.

Examples 4-6

Monomeric mixtures comprised of 2-HEMA and propylene glycol in the ratios shown in the Table were prepared and processed as in Example 1. (The concentrations of crosslinker and catalyst remained constant.).

Example 7

The formulations of Table 2 were prepared by first mixing HEMA, EGDMA, Vitamin E, BME and P-16 in the indicated proportions. The appropriate quantities of IPA and/or water were then added.

TABLE 2

| Formulation | % HEMA | % EGDMA | % Vit. E | % BME | % P-16 | % Water | % IPA |
|---|---|---|---|---|---|---|---|
| A | 78.72 | 0.40 | 0.79 | 0.24 | 0.08 | 9.89 | 9.89 |
| B | 78.72 | 0.40 | 0.79 | 0.24 | 0.08 | 19.78 | — |
| C | 68.97 | 0.35 | 0.69 | 0.21 | 0.07 | 14.85 | 14.85 |
| D | 68.97 | 0.35 | 0.69 | 0.21 | 0.07 | 29.71 | — |

Pre-determined volumes of the resulting mixtures were dispensed into glass molds and were subjected to a horizontal spin-casting process while being exposed to ultraviolet light. Upon removal of the resulting cured polymer tubes from the molds, the tubes were further dried in a vacuum oven. Drug pellets were prepared on a single station tablet press from a blend of 98% exenatide and 2% stearic acid. Drug pellets were loaded into the dried polymer tubes and the ends sealed with a monomer mixture comprised of 99.5% HEMA and 0.5% TMPTMA.

Figure 1:
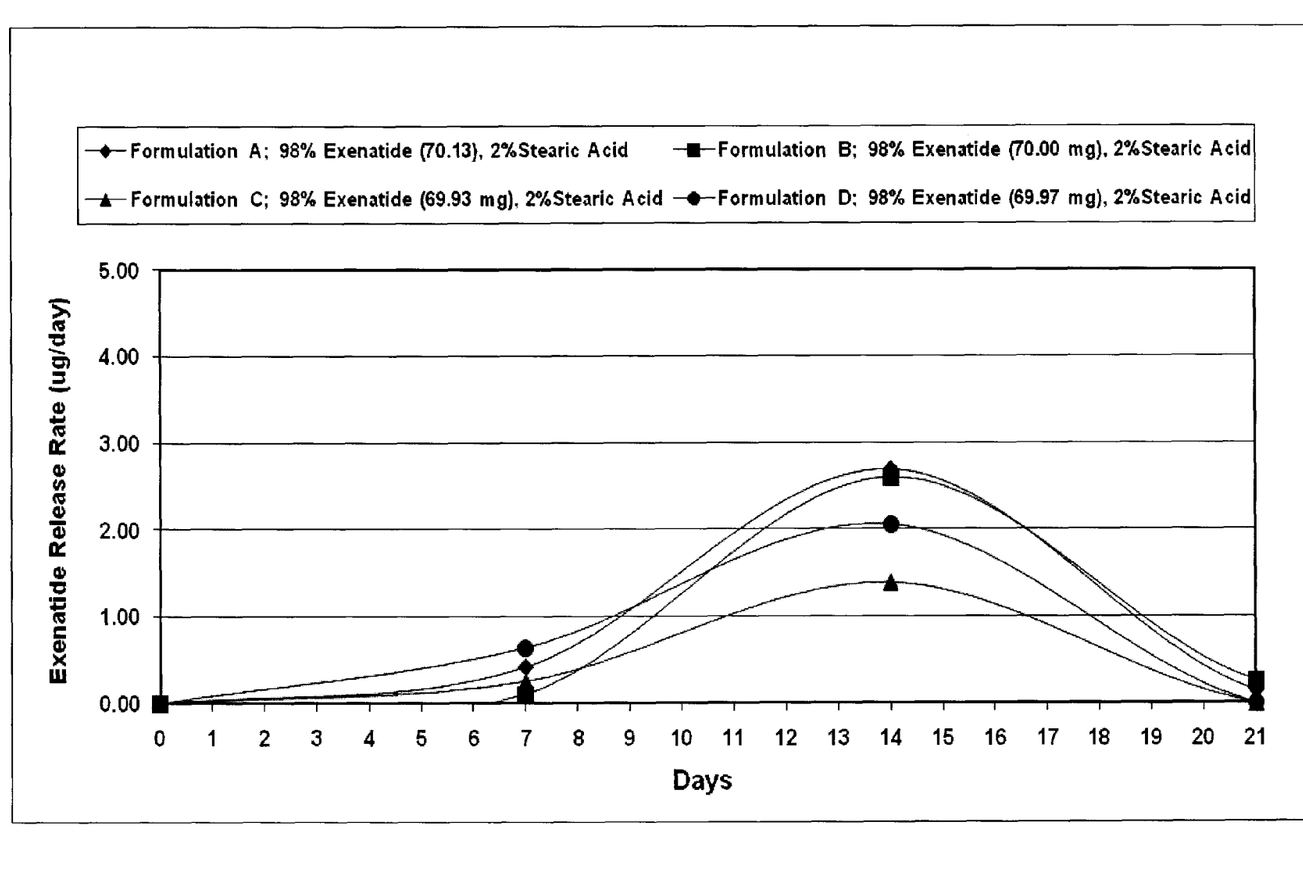
FIG. 1 is a graph showing in vitro exenatide release from four formulations as described in Example 7. HEMA: 2-hydroxyethyl methacrylate; EGDMA: ethyleneglycol dimethacrylate; TMPTMA: trimethylolpropane trimethacrylate; BME: benzoin methyl ether; P-16: Perkadox 16; WA: isopropyl alcohol.

The implants were tested in vitro for exenatide release, and the results are shown in the Figure.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A method of manufacturing an implantable device comprising: mixing one or more polymerizable monomeric substances and a release agent to form a mixture, wherein the release agent has a molecular weight ranging from about 1000 Daltons to about 2000 Daltons; placing said mixture in a mold, and polymerizing the polymerizable monomeric substances to form the implantable device.

2. The method of claim 1, wherein the one or more polymerizable monomeric substances comprises one or more compounds selected from the goup consisting of: 2-hydroxyethyl methacrylate, ethyleneglycol dimethacrylate, and trimethylolpropane trimethacrylate.

3. The method of claim 1, wherein the release agent comprises polyoxyethylene (23) lauryl ether, polyoxyetheylene (20)sorbitan trioleate, polyoxyethylene (20) sorbitan monolaurate, polyoxyethylene (20) sorbitan monooleate, or D-α-tocopheryl polyethylene glycol 1000 succinate (Vitamin E TPGS).

4. The method of claim 1, wherein the mixture further comprises one or more components selected from the group consisting of: benzoin methyl ether, di(4-tert-butylcyclohexyl) peroxydicarbonate, and isopropyl alcohol.

5. The method of claim 1 further comprising removing the implantable device from the mold after the polymerizing.

6. The method of claim 1, wherein the polymerizing comprises initiating by ultraviolet irradiation.

7. The method of claim 1 further comprising charging the implantable device with a desired amount of a therapeutic polypeptide agent.

8. The method of claim 7, wherein the therapeutic polypeptide agent is combined with a wetting agent to form a solid formulation prior to being charged into the implantable device.

* * * * *